United States Patent [19]

Voss et al.

[11] Patent Number: 4,801,587

[45] Date of Patent: Jan. 31, 1989

[54] IMPOTENCE OINTMENT

[76] Inventors: Gene Voss, 213 Alcade Moreno, San Antonio, Tex. 78232; Allen C. Eichler, 1347 Lockhill-Selma, San Antonio, Tex. 78213

[21] Appl. No.: 20,544

[22] Filed: Mar. 2, 1987

[51] Int. Cl.⁴ .................. A61K 31/47; A61K 31/50
[52] U.S. Cl. .................. 514/248; 514/307; 514/400; 514/502; 514/649; 514/947
[58] Field of Search ............ 514/307, 400, 248, 502, 514/649

[56] References Cited

U.S. PATENT DOCUMENTS

| | | |
|---|---|---|
| 1,176,597 | 3/1916 | Pictet . |
| 2,561,071 | 7/1951 | Prisk .................................. 128/260 |
| 3,795,675 | 3/1974 | Laguzzi .............................. 260/283 |
| 3,966,724 | 6/1976 | Hughes et al. ...................... 260/247 |
| 4,018,927 | 4/1977 | Vorhees .............................. 514/307 |
| 4,055,648 | 10/1977 | Sache ................................ 424/260 |
| 4,117,841 | 10/1978 | Perrotta et al. ..................... 128/155 |
| 4,311,707 | 1/1982 | Birnbaum et al. .................. 514/530 |
| 4,564,010 | 1/1986 | Coughlan et al. .................. 128/156 |

Primary Examiner—Leonard Schenkman
Attorney, Agent, or Firm—Gunn, Lee & Jackson

[57] ABSTRACT

An ointment for relieving impotence. The ointment generally consists of a primary agent, a carrier, and a base, and is applied directly to the penis. The primary agent is a vasodilator selected from the group consisting of papaverine, hydralazine, sodium nitroprusside, phenoxybenzamine and phentolamine. The carrier is used to assist absorption of the primary agent through the skin around the penis. When the primary agent enters the corpora cavernosa within the penis, it causes dilation of the corpora, resulting in an erection.

12 Claims, 1 Drawing Sheet

IMPOTENCE OINTMENT

BACKGROUND OF THE INVENTION

1. Field of the Invention

The present invention generally relates to treatment of cases of impotence among men, and more particularly to the use of a topical or intraurethral vasodilator.

2. Description of the Prior Art

Impotence, or lack of a man's ability to have sexual intercourse, is often the subject of parlor humor, but the fact is that millions of men suffer from this condition, regardless of age, place of birth, or prior sexual experience. Impotence is generally characterized by an inability to maintain a penile erection.

Causes of impotence are numerous. It may be atonic, due to paralysis of the motor nerves (nervi erigentes) without any evidence of lesion to the central nervous system. Conversely, it could be paretic as a result of a lesion in the central nervous system, particularly the spinal cord. Alternatively, it could be psychic, and dependent on a mental complex or instability. Finally, it could be symptomatic, due to some other disorder, such as injury to nerves in the perineal region, by virtue of which the sensory portion of the erection reflex is blocked out.

Obviously, the condition may be cured by eliminating the cause which lies at the root of the problem. Often, however, determining the origin of the ailment is difficult or impossible, and even if the cause is known, treatment may be ineffective.

Because of these difficulties, it would generally be acceptable to treat the malady by some artificial means of erection. Prosthetic devices have been engineered to aid stricken individuals, but these devices can be quite cumbersome and expensive. Surgery is usually required to place the prosthesis in the penis initially. Another technique involves injection of chemicals or fluids into the penis itself with a hypodermic needle, but this has obvious drawbacks.

It would therefore be desirable and advantageous to devise a method of treatment for impotence which was directed to the penis itself, but did not require intrusive and potentially painful techniques. The method should also be simple to use as well as inexpensive.

SUMMARY OF THE INVENTION

Accordingly, the primary object of the present invention is to provide a novel treatment for impotent men.

Another object of the invention is to provide treatment for impotence which works by direct application to the penis.

Still another object of the invention is to provide such treatment which will not require surgery or other costly procedures or devices.

Yet another object of the invention is to provide a method of treatment for impotence which can be performed in the privacy of one's own house, requiring no professional assistance.

The foregoing objects are achieved in a method of using a topical or intra-urethral agent on the penis. The agent may be any one of several vasodilators or alpha-blockers.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

DESCRIPTION OF THE PREFERRED EMBODIMENTS

Figure 1:
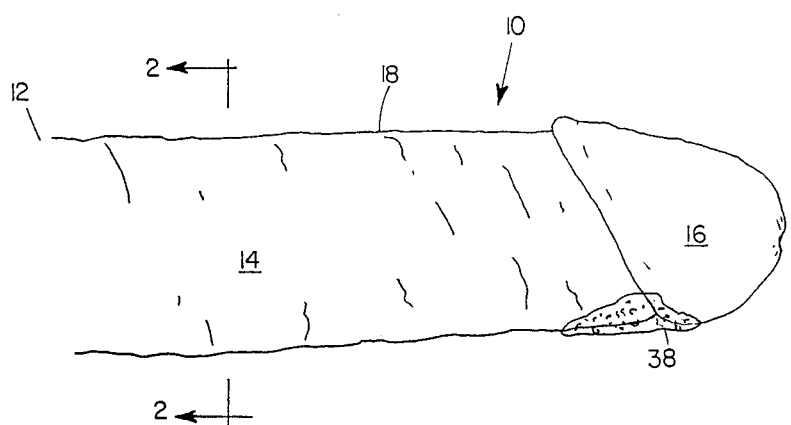
FIG. 1 is a side view of the penis depicting application of the topical agent

With reference now to the figures, and in particular with reference to FIG. 1, there is depicted a normal human penis 10. The penis generally consists of three portions, the root 12, the body 14, and the extremity or glans 16. The root 12 is firmly connected to the pelvis and ischium by two fibrous processes, the crura (not shown). The body 14 is generally cylindrical, but when erect is slightly triangular or prismatic, the upper side being the broadest, known as the dorsum 18. The glans 16 is covered with a mucous membrane and ensheathed at birth by the prepuce or foreskin, typically removed by circumcision.

Figure 2:
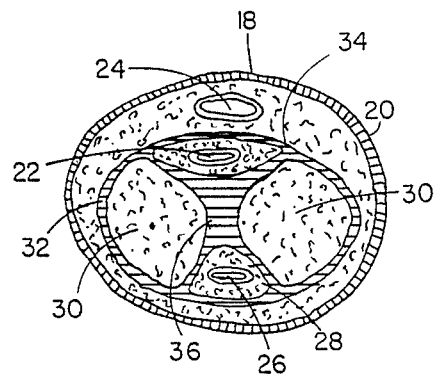
FIG. 2 is a cross-sectional view of the penis showing its inner anatomy.

With further reference to FIG. 2, the body 14 of penis 10 is surrounded by a cornified layer of skin 20. Blood is supplied through the dorsal artery 22 and removed through dorsal vein 24. The urethra 26, surrounded by a fibrous compartment 28 known as the corpus spongiosum, allows urination and provides a path for semen during ejaculation. For purposes of this application, the most important structures within the penis are the paired fibrous compartments 30 known as the corpora cavernosa.

The corpora cavernosa 30 form the chief part of the body of the penis, and at their rear portion they form the crura mentioned above. The corpora cavernosa 30 are surrounded by a fibrous sheath 32 having exterior and interior portions 34 and 36 respectively. The portion of corpora cavernosa 30 within fibrous sheath 32 consists of a sponge-like tissue of areolar spaces freely communicating with each other and filled with venous blood. This space may be thought of as a large cavernous vein. The arteries bringing blood to these spaces are the arteries of corpora cavernosa 30 and branches from the dorsal artery 22, which perforate fibrous sheath 32 along the upper surface thereof. When the corpora cavernosa 30 become swollen and congested (turgid) with blood, the result is a penile erection.

The turgor phenomenon is generally caused by an action of the autonomic nervous system. The autonomic nervous system consists of two divisions, the sympathetic nervous system and the parasympathetic nervous system. In the healthy individual, activity by one of the two autonomic nervous systems results in a physiological effect opposite to that of the activity of the other system. An autonomically-controlled physiological state is determined, at any given point in time, by the relative degree of activity of the two systems.

The autonomic system controls the blood flow in penis 10 by peripheral nerves attached to the arterial vessels in and around corpora cavernosa 30. During normal physiological activity, the sympathetic nerves maintain these arteries in a constricted state. As the man becomes aroused, his parasympathetic system releases certain chemicals, principally catecholamines such as norepinephrine and epinephrine, which inhibit the action of the sympathetic nerves, resulting in relaxation of the smooth muscles surrounding the arteries and thus dilation thereof.

Any imbalance in the autonomic system can affect this process. Mental anxiety may be the cause of this imbalance, or there may actually be damage to the central nervous system, e.g., the spinal cord. Peripheral neuropathy, which commonly afflicts diabetics or paraplegics, may inhibit the autonomic nervous system's ability to emit alpha-blockers or inhibitors within the penile arteries, resulting in impotence. No matter what the cause, however, delivery of any vasodilator within corpora cavernosa 30 can relieve this condition.

The preferred mode of application of such a vasodilator is as a topical agent, allowing absorption through the skin and into the corpora cavernosa. Because the body 14 of penis 10 has a cornified layer of skin 20, the ointment 38 should be placed near the glass 16 which, having a mucous membrane instead of a cornified layer, facilitates absorption. This is depicted in FIG. 1.

Ointment 38 generally comprises three ingredients: the primary agent, one or more carriers, and the ointment base. The primary agent can be any vasodilator or alpha-blocker. It is anticipated that papaverine (6,7-dimethoxyl-1-veratrylisoquinoline) will be the most useful in this regard. Other useful smooth muscle relaxers inclue hydralazine, sodium nitroprusside, phenoxybenzamine and phentolamine. For absorption purposes, a nonpolar, hydrophobic, or lipid soluble agent is preferred. A single application should contain between one and five milligrams of the primary agent; for example, it is anticipated that an application containing about three milligrams of papaverine would be sufficient in most cases. Depending on the total amount of ointment to be applied, the primary agent should constitute between one and five percent by weight of the mixture. Overdose should be avoided as this could result in a painful sustained erection, possibly even ischemia.

Carriers include any substances which may remain transdermal delivery of the primary agent. If the primary agent is already easily absorbed through the skin, then a carrier may be unnecessary. The best carrier is probably dimethyl sulfoxide (DMSO), but others, such as glycerin or lanolin, may be used. The primary agent and carrier may be conveniently suspended in a petroleum base. The base may contain preservatives or other ancillary ingredients.

Alternatively, the agent may be applied in a layered manner. This technique would require that the user first place an ointment having only the carrier therein on the glans 16, and allowing it to remain there for a few minutes. It would then be wiped off, and a second ointment applied which contained the primary agent. The initial presence of the carrier provides a physiological pathway of absorption for the agent to follow.

Figure 3:
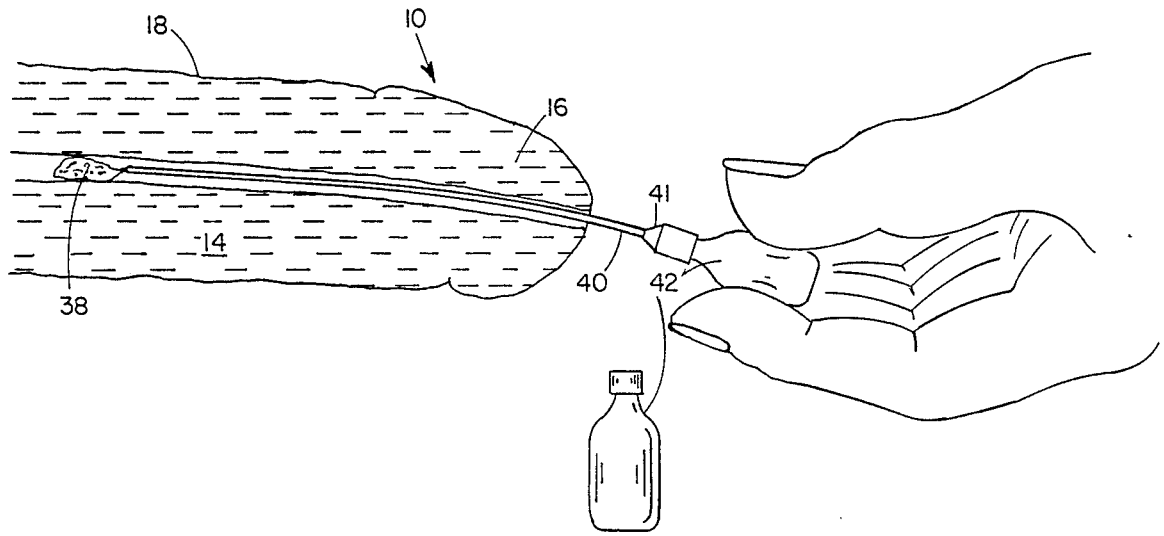
FIG. 3 is a longitudinal cross-section of the penis depicting the intraurethral method of application of the agent.

A third method of applying the agent is depicted in FIG. 3. It comprises the steps of placement of a catheter 40 within the urethra 26, followed by introduction of ointment 38 therein. After catheter 40 has been placed within urethra 26, a tube 42 may be attached thereto; catheter 40 may be equipped with a threaded end 41 to mate with the open end of tube 42. The tubes 42 may each conveniently contain a single dosage. After a few minutes, excess ointment within the urethra may be expelled by squeezing or urination.

In addition to the above-described techniques, it may be desirable to surgically remove a portion of the fibrous sheath 32 surrounding corpora cavernosa 30. This would enhance the absorption of the vasodilator into the copora. The surgery would only be necessary once, as the fibrous sheath 32 does not regenerate.

Although the invention has been described with reference to specific embodiments, this description is not meant to be construed in a limiting sense. Various modifications of the disclosed embodiment, as well as alternative embodiments of the invention will become apparent to persons skilled in the art upon reference to the description of the invention. It is therefore contemplated that the appended claims will cover such modifications that fall within the true scope of the invention.

I claim:

1. A method of relieving impotence comprising the single step of applying an ointment to the skin around the penis, said ointment comprising:
    a primary agent, being a vasodilator, selected from the group consisting of papaverine, hydralazine, sodium nitroprusside, phenoxybenzamine or phentolamine, said primary agent being present in said ointment in an amount between one and five percent by weight;
    dimethyl sulfoxide for assisting absorption of said primary agent through said skin; and
    a base.

2. The method of claim 1 wherein said ointment is applied to the glans portion of the penis.

3. A method of relieving impotence comprising the steps of:
    applying a first ointment to the skin around the penis, said first ointment containing only a carrier for assisting absorption of a primary agent through said skin;
    removing said first ointment from said skin after a short period of time; and
    applying a second ointment to said skin said second ointment containing said primary agent, wherein said primary agent is selected from the group consisting of papaverine, hydralazine, sodium nitroprusside, phenoxybenzamine and phentolamine, and said primary agent is present in said second ointment in an amount between one and five percent by weight.

4. The method of claim 3 wherein said carrier is dimethoxy sulfoxide.

5. The method of claim 3 wherein said first and second ointments are applied to the glans portion of said penis.

6. A method of relieving impotence comprising the steps of:
    placing a catheter within the urethra of the penis, said catheter being in fluid communication with a tube, said tube containing an ointment, said ointment comprising a primary agent and a base, wherein said primary agent is a vasodilator and is present in an amount of between one and five percent by weight; and
    squeezing said tube thereby extruding said ointment into said catheter and into said urethra.

7. The method of claim 6 wherein said primary agent is selected from the group consisting of papaverine, hydralazine, sodium nitroprusside, phenoxybenzamine and phentolamine.

8. The method of claim 6 wherein said ointment further comprises a carrier for assisting absorption of said primary agent through the wall of said urethra.

9. The method of claim 8 wherein said carrier is dimethoxy sulfoxide.

10. A method of relieving impotence comprising the steps of:
   surgically removing a portion of the fibrous sheath surrounding the corpora cavernosa within the penis; and
   applying an ointment to the skin around said penis, said ointment comprising a primary agent, being a vasodilator, and a base, said primary agent being present in an amount of between one and five percent by weight.

11. The method of claim 10 wherein said primary agent is selected from the group consisting of papaverine, hydralazine, sodium nitroprusside, phenoxybenzamine and phentolamine.

12. The method of claim 10 wherein said ointment further comprises a carrier for missing absorption of said primary agent through the wall of said urethra.

* * * * *